United States Patent [19]

Butler et al.

[11] Patent Number: 5,056,530
[45] Date of Patent: Oct. 15, 1991

[54] METHOD OF MEASURING AXIAL FORCE IN MAMMALIAN FIBROUS TISSUE AND DEVICE

[75] Inventors: David L. Butler, Fairfield; Edward S. Grood, Cincinnati; Donald C. Stouffer, Cincinnati; David L. Glos, Cincinnati, all of Ohio

[73] Assignee: University of Cincinnati, Cincinnati, Ohio

[21] Appl. No.: 284,949

[22] Filed: Dec. 15, 1988

[51] Int. Cl.[5] ............................................. A61B 5/103
[52] U.S. Cl. ..................................... 128/774; 128/782
[58] Field of Search ........ 128/774, 782, 903, 887–888, 128/748; 338/2, 6

[56] References Cited

U.S. PATENT DOCUMENTS

| | | | |
|---|---|---|---|
| 3,905,356 | 9/1975 | Fletcher et al. | 128/774 X |
| 4,209,859 | 7/1980 | Hoffman . | |
| 4,294,015 | 10/1981 | Drouin et al. . | |
| 4,301,551 | 11/1981 | Dore et al. . | |
| 4,693,606 | 9/1987 | Podolsky et al. . | |
| 4,739,751 | 4/1988 | Sapega et al. . | |
| 4,813,435 | 3/1989 | Arms | 128/774 |

FOREIGN PATENT DOCUMENTS

| | | |
|---|---|---|
| 0169045 | 1/1986 | European Pat. Off. . |
| 8705789 | 3/1987 | PCT Int'l Appl. . |
| 2061532 | 5/1981 | United Kingdom . |

OTHER PUBLICATIONS

Lewis et al., Journal of Biomechanical Engineering, vol. 104, May 1982, pp. 125–128.
Fischer et al., The American Journal of Sports Medicine, vol. 13, No. 6, pp. 390–397, 1985.
Edwards et al., Journal of Basic Engineering, Mar. 1970, pp. 131–135.
France et al., J. Biomechanics, vol. 16, No. 8, pp. 553–564, 1983.
White et al., Acta Orthop. Scandinav. 43, 176–187, 1972.
Lewis et al., In Vivo Forces in the Collateral Ligaments of Canine Knees, 27th Annual ORS, Neveda, 2/81, pp. 4, 241 & 301.
Arms et al., "The American Journal of Sports Medicine", vol. 12, No. 1, pp. 8–17, 1984.

Primary Examiner—Lee S. Cohen
Assistant Examiner—John P. Lacyk
Attorney, Agent, or Firm—Wood, Herron & Evans

[57] ABSTRACT

A method of detecting axial force in human and animal fibrous tissue such as ligaments, tendons and muscle tissue employs an implantable force transducer or IFT which measures lateral compressive forces as axial force is applied to the fibrous tissue. The lateral compressive forces are proportional to the axial force. Preferably the device is a curved clip formed from a band of spring steel utilizing bonded strain gages. This device is connected to a Wheatstone bridge circuit to detect flexure of curved metal clip. The device is suitable for in vivo and in vitro use.

9 Claims, 3 Drawing Sheets

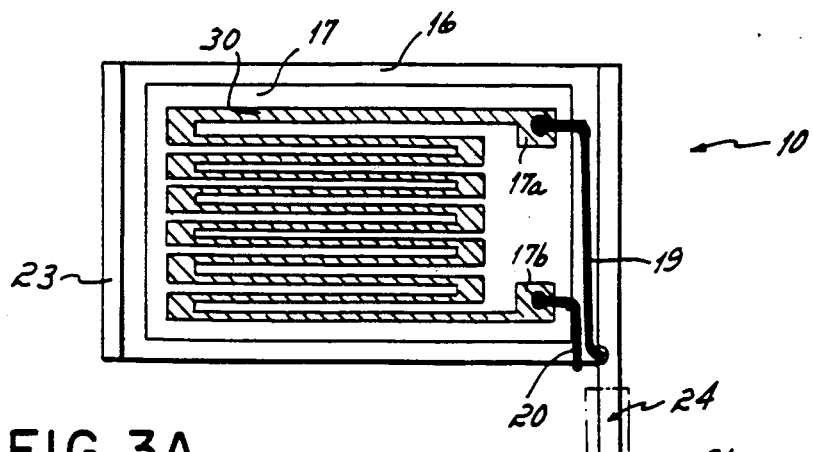
FIG. 3A
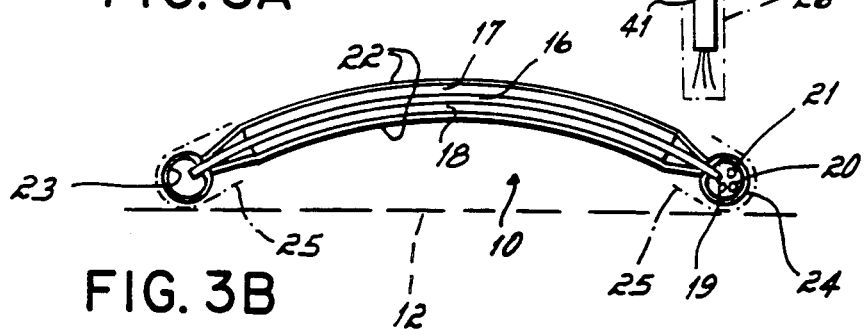
FIG. 3B
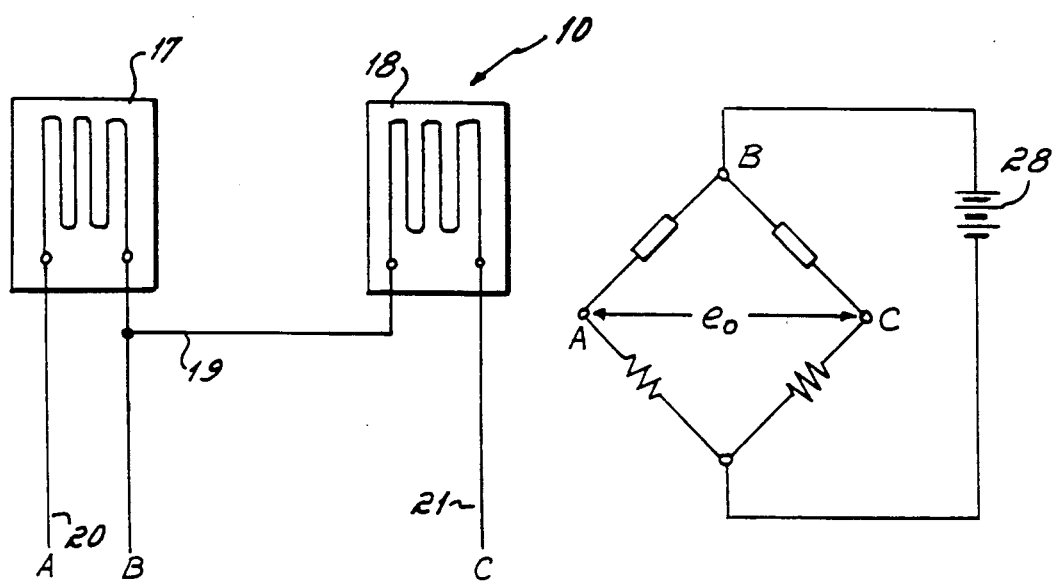
FIG. 4A
FIG. 4B

METHOD OF MEASURING AXIAL FORCE IN MAMMALIAN FIBROUS TISSUE AND DEVICE

BACKGROUND OF THE INVENTION

The number of ligament and tendon injuries continues to increase each year. It is estimated, for example, that over 250,000 knee sprains occurred in 1984 alone These injuries also remain difficult to repair and reconstruct. While many would debate about the mechanics of the soft tissue injuries and about the efficacy of surgical treatment of these tissues, most would agree that the surgical results could be improved if the level of force placed on these tendons could be measured and controlled.

Measuring ligament and tendon forces has also been difficult. Many techniques have been tried, some in vivo but most in vitro. These techniques have included use of buckle gages, liquid metal strain gages, Hall sensors and clip gages attached directly to the tissue or adjacent to the tissue's insertion into bone.

Buckle gages have been employed by many investigators studying the characteristics of tendons in vivo; ligaments have been examined both in vitro and more recently in vivo. The buckle gage has a rectangular frame with cross bar between two sides of the frame. The tissue is folded into the buckle frame and the cross bar positioned between the two frame members. As tension increases on the ligament, the buckle frame is deflected producing a output proportional to the tissue load.

While this technique is believed to be most directly related to average axial tissue force and to work reasonably well in long tendons, it has several disadvantages. Buckle gages can induce significant shortening in shorter ligaments and tendons. They can also impinge upon the surrounding soft tissues and bone since they are surface mounted.

Others have attached liquid metal strain gages and Hall effect strain transducers to try and measure forces in tendons and ligaments. These displacement measuring devices have many of the same problems. Each one is surface mounted so that impingement can again be a problem. The liquid metal strain gages contain toxic heavy metals which make them unsuitable for long term in vivo use. These attach to the soft tissue fibers. The Hall effect devices have several problems. First they have no measurable stiffness so it is difficult to correlate their displacement with tissue load. Second, they have a very small linear operating range. Third, with both devices, force must be inferred from tendon or ligament deformation via nonlinear time dependent constitutive properties. Finally, the initial length of these devices when the tissue first develops load must be known before strain and thus stress and force can be determined.

Two other less utilized methods have been described. Anterior cruciate ligament deformation under the tibial insertion site has been reported in two patients. Displacement of the insertion was measured using a strain transducer positioned in a tibial drill hole co-linear with the ligament. The technique unfortunately may compromise the normal ligament attachment to the bone. In the other method, ligament force was measured by recording bone displacement adjacent to the insertion site. Measuring bone strain, however, is demanding because the gages can be difficult to attach near the tissue insertion site. Also a substrate has to be placed on the bone at the insertion possibly compromising the structural integrity of the tissue insertion. Further, gage output during in vitro or in vivo use may come from deformations in surrounding tissues or from weight bearing or muscle forces unrelated to the ligament loads.

While these methods have improved our understanding of tendon and ligament function, a less obtrusive and more direct method is now needed to measure soft tissue force.

SUMMARY OF THE INVENTION

Accordingly, it is an object of the present invention to provide a method to measure axial force in fibrous tissue such as ligaments, tendons, muscles, or even skin wherein the measuring device is inserted within the tissue being measured.

Further, it is an object of the present invention to measure axial force in the tissue by measuring the lateral compressive forces imposed on the device by deflected tissue fibers during tissue deformation.

Further it is an object of the present invention to rely on lateral compressive forces acting against a contoured strain measuring element whereby the strain developed in this element relates uniquely to axial tissue force.

Accordingly, it is an object of the present invention to provide a strain measuring device implanted within the tissue which would minimally displace fibers of the tissue when inserted. The device can be a curved strain-measuring element adapted for implantation within the body for in vivo applications.

The present invention will be further appreciated in light of the following detailed description and drawings wherein:

BRIEF DESCRIPTION OF THE DRAWINGS

FIGS. 3A and 3B show top and side views of the IFT for use in the present invention.

FIGS. 4A and 4B are electrical wiring diagrams showing the circuitry of the IFT and the circuitry used to measure output of an IFT used in the present invention.

FIG. 5 is a graph showing the results of a cyclic loading test as measured in accordance with the example. The voltage from the IFT has been scaled by a constant factor so the peak voltages are similar.

DETAILED DESCRIPTION OF THE INVENTION

Figure 1A:
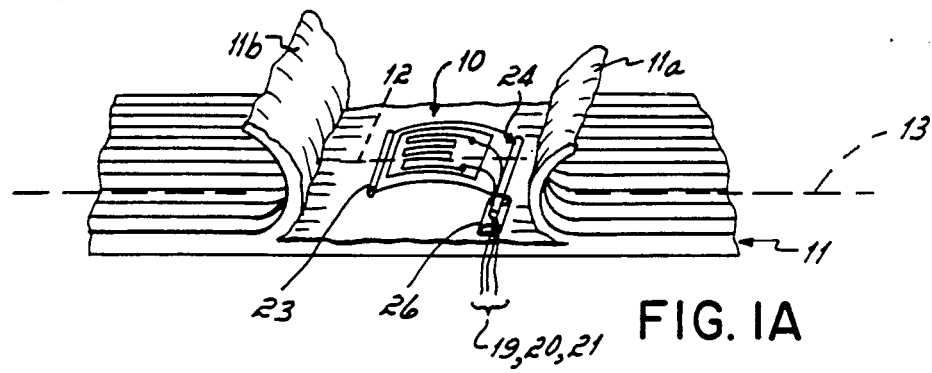
FIGS. 1A and 1B show perspective and diagrammatic cross-sectional views of a tendon incorporating an implantable force transducer (IFT) according to the present invention. In FIG. A a portion of the tendon is pulled away to display the IFT.
Figure 1B:
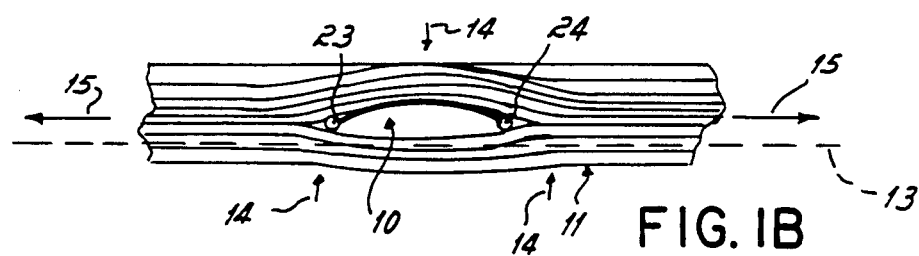

According to the present invention, an internal force transducer (IFT) 10 is implanted within a fibrous tissue. As shown in FIGS. 1A and 1B the fibrous tissue is a tendon 11 with the IFT located totally surrounded by the tendon tissue. In FIG. 1A portions 11a and 11b of the tendon are shown separated and pulled up merely to show the location of the IFT. In use the IFT would be implanted as shown in FIG. 1B.

The long axis shown by dashed line 12 of the IFT is preferably aligned with the long axis 13 of the tendon 11. In this manner lateral compressive force shown by arrows 14 will act on the IFT tending to flatten it out as axial force (shown by arrows 15) is applied to the tendon.

Figure 2:
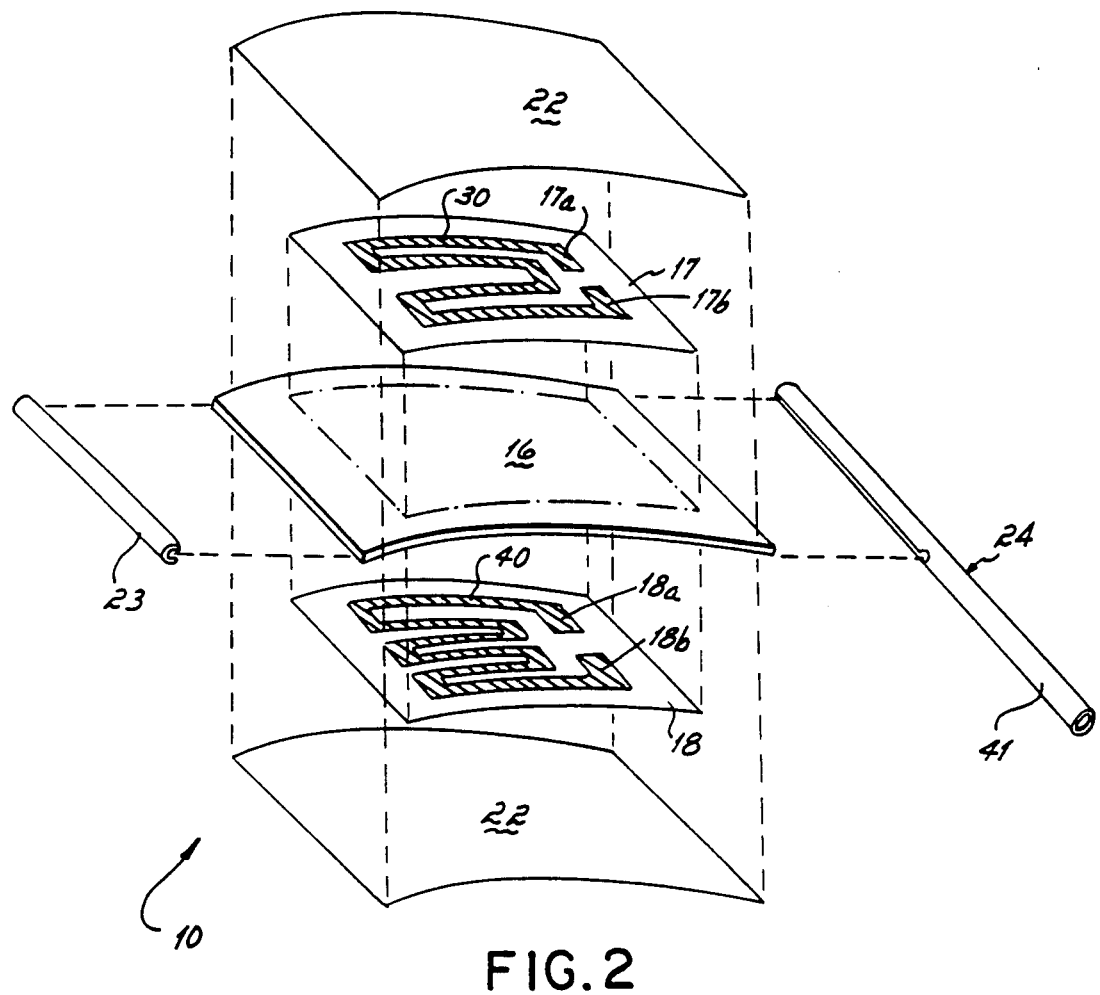
FIG. 2 is an exploded view of an IFT for use in the present invention.

The IFT can be made from a variety of different materials and in a variety of different manners. The general requirement is that it measure lateral compressive force within fibrous tissue. Therefore it will generally be a device constructed such that application of axial forces will tend to alter its geometry. The IFT 10 shown in FIGS. 3A and 3B includes a central spring steel clip 16 which has a curved contour. On either side of clip 16 are first planar axial strain gage 17 and second axial strain gage 18. A first jumper wire 19 (see FIG. 4A) connects the first and second strain gages 17 and 18 at a first end of each 17a and 18a. Wires 20 and 21 are connected to strain gages 17 and 18 at ends 17b and 18b as shown in FIG. 2. Shaded areas 30 and 40 of gages 17 and 18 are resistors. Thus stretching or compressing gages 17 and 18 alter the configuration of resistors 30 and 40 and thus the resistance from points 18a to 18b or 17a to 17b. The strain gages can be purchased, for example, from Micromeasurements, Inc.

The entire device is coated with for example a silicone or Teflon coating 22 which prevents bodily fluids from contacting any of the wires or resistors which would have an effect of shorting these out.

To form the IFT 10 the clip 16 is cut from curved spring steel to a desired size. Protective rails (1/16" OD copper tubing) 23 and 24 are soldered to each end thereof. The entire device is then cleaned with sand and acid etched. Tube 14 is slightly longer than the lateral width of the IFT 10 so that a portion 41 extends beyond the edge of clip 16. Strain gages 17 and 18 are then bonded to either side of the clip with an adhesive. Each of these gages has the same resistances typically either 120 or 350 ohm. Wires are run through tubing 24 and soldered to ends 17a, 17b, 18a and 18b as set forth in FIG. 4A. The entire device is then cleaned with a rosin solvent and baked at 200° F. for two hours. Teflon layers 22 are bonded above and below the device and the edges trimmed. The device is then cleaned with a solvent again and baked as before and subsequently coated with polyurethane 25. A short piece of shrink tubing 26 (FIG. 1A) is applied to copper tube 24 for strain relief. The wires 19, 20 and 21 are then coated with medical grade silicone elastomer.

The strain gages are applied to the unloaded IFT. These two active gages are networked with two balancing resistors in what is commonly called a Wheatstone bridge. Applications of transverse load to the IFT produce tensile strains on one surface of the IFT clip and compressive strains on the other surface. The resistance of the strain gages changes when tensile or compressive strains are applied thus changing the balance of the bridge which is indicated by a voltage change, $e_0$ (see FIG. 4B).

The curved metal clip 16 is preferably a thin metallic member having a thickness of about 0.1 mm to about 0.5 mm, a width of from about 2 mm to 6 mm and a length of 4 mm to 12 mm. The actual dimensions will vary widely depending on the transverse force measured. If the transverse forces measured in the tissue are relatively small the clip would have to be thinner to maintain adequate sensitivity. If the device is implanted in a tendon where the transverse forces are relatively large a less flexible clip would be used. It is necessary that the transverse force imposed upon the IFT not totally flatten clip 16. The flattened position is obviously the limit of the IFT. Generally the voltage source 28 will have an applied voltage of 0 to 5V. This is not significant relative to the current circuitry.

Other strain measuring devices could be used in place of the IFT described above. For example capacitive strain gages as well as piezo resistive strain gages could be employed. The critical feature for the (strain gage) implantable force transducer is that it must measure lateral compressive force. Preferably it will be a device which bends when lateral compressive force is applied as opposed to a device such as a tubular device which would constrict as lateral compressive forces are applied. The benefit of having a device which flexes upon application of lateral compressive force is that it requires less force to provide a detectable output and provides for easier calibration of the device over a wider range of forces.

Also contemplated within the scope of the present invention are devices which, instead of using actual leads which come out of the body are telemetric systems which require no such lead wires.

Depending on the size and shape of the device, it can be implanted with a variety of different methods either using arthroscopic surgical tools or simply using a scalpel to cut a slit slightly larger than IFT 10 partially through the tendon. The slit would be parallel to the long axis of the tendon. The IFT would be pushed into the slit with a portion of tube 24 extending out of the tendon. The slit would be sutured closed holding the IFT in place.

To test the present invention an IFT as shown in FIG. 3 was inserted into a human cadaveric patellar tendon. The tissue was mounted in an Instron 1321 mechanical testing system with one end attached to a load cell and the other to an actuator capable of extending the tissue. The voltage outputs of the load cell and IFT were compared.

Figure 5:
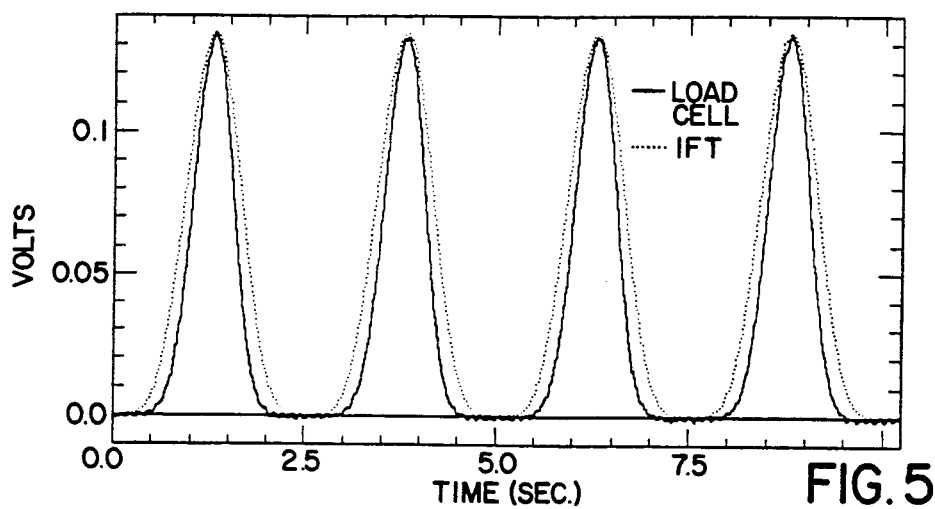

The output voltages of the IFT and load cell during cyclic loading of the tendon to 300 pounds peak force are compared in FIG. 5. The IFT tracks the load cell response over a frequency range of 0.1–20 Hz. The voltage for the IFT has been scaled by a constant factor so the peak voltages are similar.

Figure 6:
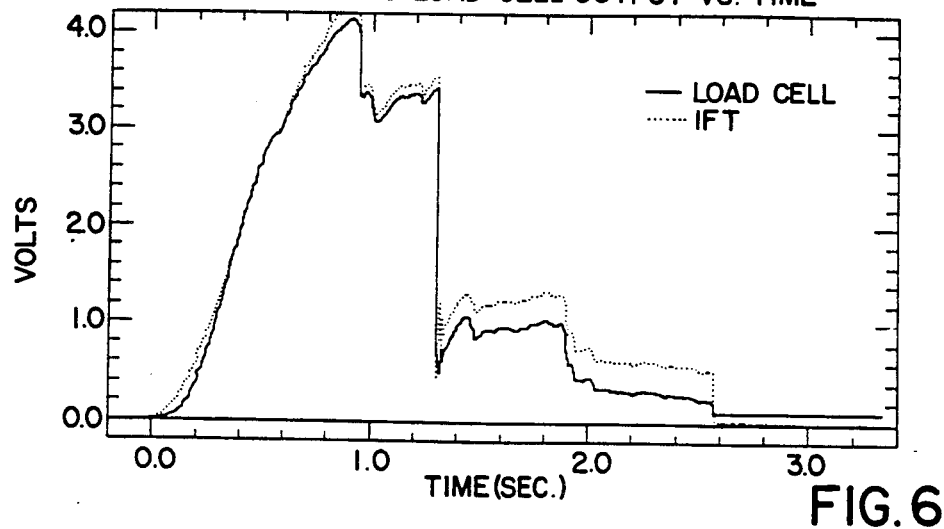
FIG. 6 is a graph of failure force in the tissue measured by an in line load cell and the IFT.

As shown in FIG. 6, the tendon was then failed at a very fast rate (100%/sec strain rate) and the IFT and load cell responses compared. The IFT tracked the load cell output up to a maximum load of 2400N and during the serial failure process beyond maximum force. This has never been demonstrated before.

Figure 7:
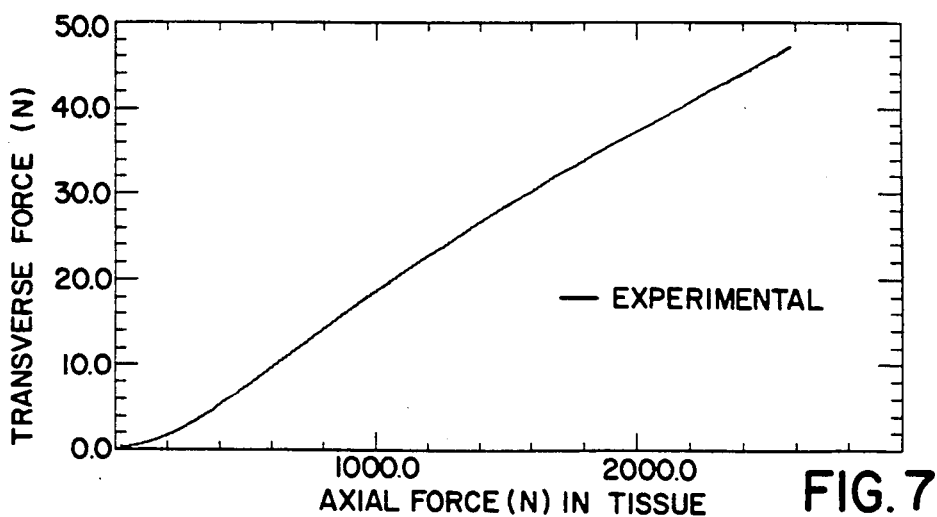
FIG. 7 is a graph of transverse force on the IFT versus average axial tissue force as measured in accordance with the device.

The transverse load on the IFT was directly plotted against the load cell output during the failure test (FIG. 7). Note the nearly linear relationship between the output of the two devices. This relationship is unique.

The data from this experiment demonstrates that the implantable force transducer (IFT) or device 10 described above accurately indicates axial force applied to a fibrous tissue by measuring lateral compressive force. The direct relationship between axial force and compressive force is an accurate means to determine axial force.

Further since the device can be totally implanted within the fibrous tissue and is not attached to the exterior of the tissue it can permit the fibrous tissue to function without significant interference. This permits the present device to be used in a variety of in vivo uses, such as the long term measurement of axial forces on a tendon, ligament or muscle. Its accuracy permits it to be used in surgical procedures where torn tendons and ligaments are repaired. Other potential applications would include implantation in tendons of disabled patients to measure muscle forces, implantation in synthetic ligaments to control the force levels at the time of surgery, and possibly in the muscles of astronauts to monitor the effects of disuse in a zero-gravity environment.

The preceding has been a description of how to practice the present invention along with the preferred embodiment of the present invention.

However, the invention is defined by the following claims wherein we claim:

1. A method of measuring axial force in fibrous tissue comprising implanting a flexible arcuate member completely within said tissue in a position whereby lateral compressive forces generated by said axial force act to flatten said arcuate member;
    measuring flattening of said arcuate member caused by said lateral compressive forces to thereby provide an indication of said axial force.

2. The method claimed in claim 1 wherein said tissue is tendon.

3. The method claimed in claim 1 wherein said tissue is ligament.

4. The method claimed in claim 1 wherein said tissue is muscle tissue.

5. The method claimed in claim 1 wherein said tissue is skin.

6. An implantable force transducer adapted to be located within the interior of and surrounded by fibrous tissue comprising an arcuate member having upper and lower surfaces, a first strain gauge bonded to said upper surface, a second strain gauge bonded to said lower surface whereby flattening of said arcuate member generates detectable outputs from said first and second strain gauges to thereby provide a measurement of force acting to flatten said arcuate member.

7. The implantable force transducer claimed in claim 6 wherein said arcuate member has a generally rectangular configuration.

8. A method of measuring axial force in fibrous tissue comprising implanting an internal force transducer totally within said tissue by cutting a slit between fibers in said tissue, inserting said internal force transducer within said slit and suturing said slit closed thereby holding internal force transducer in place, measuring deflection of said internal force transducer caused by lateral compressive forces generated by application of axial force on said tissue.

9. The method claimed in claim 8 wherein said internal force transducer detects flexing of said internal force transducer along an axis of said internal force transducer, said method further comprising positioning said internal force transducer in said tissue with said axis aligned with fibers in said fibrous tissue.

* * * * *